US009109994B2

(12) United States Patent
Casasanta, III

(10) Patent No.: US 9,109,994 B2
(45) Date of Patent: Aug. 18, 2015

(54) INELASTIC ELECTRON TUNNELING AIR MONITOR

(75) Inventor: Vincenzo Casasanta, III, Woodinville, WA (US)

(73) Assignee: Empire Technology Development LLC, Wilmington, DE (US)

( * ) Notice: Subject to any disclaimer, the term of this patent is extended or adjusted under 35 U.S.C. 154(b) by 371 days.

(21) Appl. No.: 13/642,018

(22) PCT Filed: Apr. 9, 2012

(86) PCT No.: PCT/US2012/032751
§ 371 (c)(1), (2), (4) Date: Oct. 18, 2012

(87) PCT Pub. No.: WO2013/154524
PCT Pub. Date: Oct. 17, 2013

(65) Prior Publication Data

US 2013/0263646 A1 Oct. 10, 2013

(51) Int. Cl.
*G01N 27/12* (2006.01)
*G01N 27/00* (2006.01)

(52) U.S. Cl.
CPC .............. *G01N 27/00* (2013.01); *G01N 27/125* (2013.01); *Y10T 29/49002* (2015.01)

(58) Field of Classification Search
CPC .... G01N 1/2214; G01N 27/00; G01N 27/125
USPC ............. 73/31.01, 31.05, 31.06; 96/108, 143, 96/154
See application file for complete search history.

(56) References Cited

U.S. PATENT DOCUMENTS

| | | | | |
|---|---|---|---|---|
| 4,836,012 | A * | 6/1989 | Doty et al. | 73/31.06 |
| 6,171,378 | B1 | 1/2001 | Manginell et al. | |
| 8,127,595 | B2 * | 3/2012 | Finlay et al. | 73/31.07 |
| 2004/0110300 | A1 | 6/2004 | Carpenter | |

OTHER PUBLICATIONS

Blanco, F. et al., Fabrication and Characterisation of microporous activated carbon-based pre-concentrators for benzene vapours, Science Direct, Sensors and Actuators B, 2008, 90-98, 132.

(Continued)

*Primary Examiner* — Hezron E Williams
*Assistant Examiner* — David Z Huang
(74) *Attorney, Agent, or Firm* — Moritt Hock & Hamroff LLP; Steven S. Rubin, Esq.

(57) ABSTRACT

Technologies are generally described for an air monitoring device, a method for forming an air monitoring device, and methods and systems for monitoring air using an air monitoring device. A method of forming an air monitor device may include placing a sorbent membrane on a material of n type conductivity. The method may further include placing an electrode on the membrane and placing a thermoelectric heater in thermal communication with the membrane. The method may further include placing the membrane, material, and electrode in a sealed container including a valve to form the air monitor device. The valve may be effective to selectively expose the membrane to an environment outside of the container.

19 Claims, 5 Drawing Sheets

(56) References Cited

OTHER PUBLICATIONS

Mazeina, L. et al., Interaction of functionalized Ga2O3 NW-based room temperature gas sensors with different hydrocarbons, Sensors and Actuators B, 2010, 114-120, 151.

Hipps, K.W. and U. Mazur, Inelastic Electron Tunneling Spectroscopy, Handbook of Vibrational Spectroscopy, 2002, 19 pages.

Bommisetty, V., Gas Sensing Based on Inelastic Electron Tunneling Spectoscopy, IEEE Sensors Journal, 2008, 983-988, vol. 8, 6.

Taniguchi, M. et al., Inelastic electron tunneling spectroscopy of single-molecule junctions using a mechanically controllable break junction, Nanotechnology, 2009, 1-8, 20.

Behanan, R., A gas sensor based on inelastic electron tunneling spectroscopy for electronic nose applications, South Dakota State University, 2005, 144 pages.

International Search Report and Written Opinion for application with No. PCT/US2012/032751 dated May 30, 2012, 4 pages.

* cited by examiner 100
102
104
106a
106b
106c
108
110
112
112a
114
116
118
120
122
124
124a
126
128
130
132
134
136
138
140
142
144
146
148
150
180
182
184
186

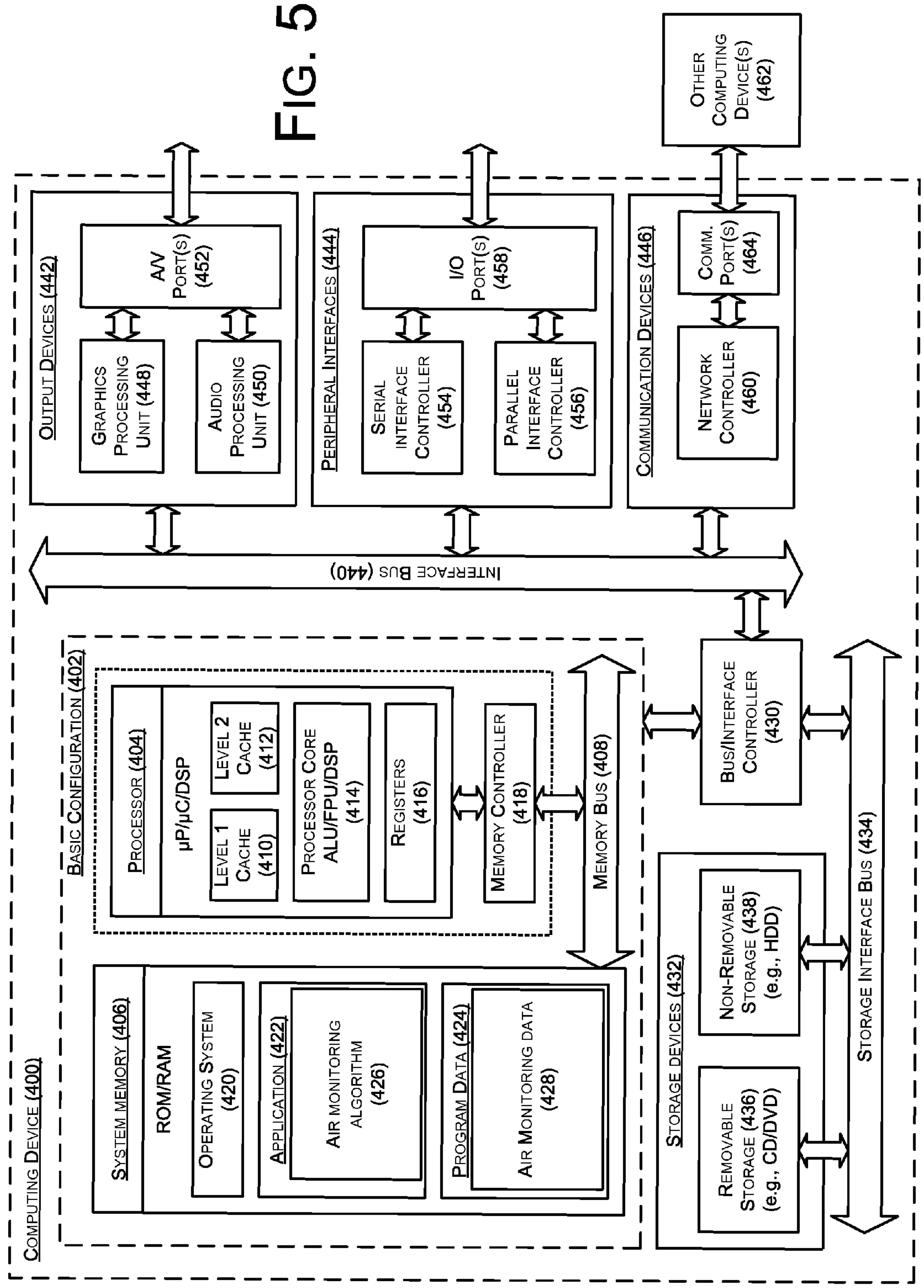
FIG. 5
Computing Device (400)
Basic Configuration (402)
Processor (404)
µP/µC/DSP
Level 1 Cache (410)
Level 2 Cache (412)
Processor Core ALU/FPU/DSP (414)
Registers (416)
Memory Controller (418)
Memory Bus (408)
System Memory (406)
ROM/RAM
Operating System (420)
Application (422)
Air monitoring algorithm (426)
Program Data (424)
Air Monitoring data (428)
Bus/Interface Controller (430)
Storage devices (432)
Removable Storage (436) (e.g., CD/DVD)
Non-Removable Storage (438) (e.g., HDD)
Storage Interface Bus (434)
Interface Bus (440)
Output Devices (442)
Graphics Processing Unit (448)
Audio Processing Unit (450)
A/V Port(s) (452)
Peripheral Interfaces (444)
Serial Interface Controller (454)
Parallel Interface Controller (456)
I/O Port(s) (458)
Communication Devices (446)
Network Controller (460)
Comm. Port(s) (464)
Other Computing Device(s) (462)

INELASTIC ELECTRON TUNNELING AIR MONITOR

CROSS REFERENCE TO RELATED APPLICATIONS

This application is a U.S. national stage filing under 35 U.S.C. §371 of International Application No. PCT/US2012/032751 filed Apr. 9, 2012, the entirety of which is hereby incorporated by reference.

BACKGROUND

Unless otherwise indicated herein, the materials described in this section are not prior art to the claims in this application and are not admitted to be prior art by inclusion in this section.

In inelastic electron tunneling spectroscopy, electrons may be sent from a source electrode through a material to a destination electrode. A fraction of the electrons tunneling through the material may lose part of their energy by exciting vibronic states of molecules in the material. These lost electrons may be measured to determine a fingerprint of the material.

SUMMARY

In some examples a method of forming an air monitor device is generally described. The method may include placing a sorbent membrane on a material of n type conductivity. The method may further include placing an electrode on the membrane. The method may further include placing a thermoelectric heater in thermal communication with the membrane. The method may further include placing the membrane, material, and electrode in a sealed container including a valve to form the air monitor device. The valve may be effective to selectively expose the membrane to an environment outside of the container.

In some examples an air monitor device is generally described. The air monitor device may include a sorbent membrane on a material of n type conductivity. The air monitor device may further include an electrode on the membrane. The air monitor device may further include a thermoelectric heater in thermal communication with the membrane. The air monitor device may further include the membrane, n type material, and electrode in a sealed container. The sealed container may include a valve effective to selectively expose the membrane to an environment outside of the container.

In some examples, a method for monitoring air using an air monitoring device is generally described. The method may include opening a valve of the air monitoring device. The method may further include heating a sorbent membrane of the air monitoring device sufficient to at least partially liberate a substance in the membrane. The method may include closing the valve. The method may further include applying a first voltage across the membrane. The method may include detecting a first current through the membrane while the first voltage is applied across the membrane. The method may further include determining a first fingerprint of the membrane based on the first voltage and first current. The method may include opening the valve. The method may further include sorbing an analyte from the air in the membrane. The method may include closing the valve. The method may further include applying a second voltage across the membrane. The method may include detecting a second current through the membrane while the second voltage is applied across the membrane. The method may further include determining a second fingerprint of the membrane with the analyte based on the second voltage and second current. The method may include subtracting the first fingerprint from the second fingerprint to determine a third fingerprint of the analyte. The method may include comparing the third fingerprint of the analyte with a library of fingerprints to identify the analyte.

In some examples, a system effective to monitor air is generally described. The system may include an air monitor device, a sealed container, a thermoelectric heater, a power source, a current measuring device and a processor. The air monitor device may include a sealed container including a valve and a sorbent material. The may be effective to selectively expose the sorbent material to an environment outside of the container. The thermoelectric heater may be in thermal communication with the membrane. The power source may be in communication with the membrane. The current measuring device may be in communication with the membrane. The processor may be in communication with the valve, the thermoelectric heater, the power source and the current measuring device. The processor may be effective to control the valve to open. The processor may be effective to control the thermoelectric heater to heat the sorbent membrane of the air monitoring device sufficient to at least partially liberate a substance in the membrane. The processor may be effective to control the valve to close. The processor may be further effective to control the power source to apply a first voltage across the membrane. The processor may be effective to control the current measuring device to detect a first current through the membrane while the first voltage is applied across the membrane. The processor may be effective to determine a first fingerprint of the membrane based on the first voltage and the first current. The processor may be effective to control the valve to open so that the membrane sorbs an analyte from the air. The processor may be further effective to control the valve to close. The processor may be effective to control the power source to apply a second voltage across the membrane. The processor may be effective to control the current measuring device to detect a second current through the membrane while the second voltage is applied across the membrane. The processor may be effective to determine a second fingerprint of the membrane with the analyte based on the second voltage and second current. The processor may be further effective to subtract the first fingerprint from the second fingerprint to determine a third fingerprint of the analyte. The processor may be effective to compare the third fingerprint of the analyte with a library of fingerprints to identify the analyte.

In some examples, a method for monitoring air using an air monitoring device is generally described. The method may include opening a valve of the air monitoring device. The method may include sorbing an analyte from the air in the membrane. The method may further include closing the valve. The method may include applying a voltage across the membrane. The method may further include detecting a current through the membrane while the voltage is applied across the membrane. The method may include determining a fingerprint of the membrane with the analyte based on the voltage and current. The method may further include subtracting the first fingerprint from a fingerprint of the membrane to determine a fingerprint of the analyte. The method may include comparing the fingerprint of the analyte with a library of fingerprints to identify the analyte.

In some examples, a system effective to monitor air is generally described. The system may include an air monitor device, a sealed container, a thermoelectric heater, a power source, a current measuring device and a processor. The air monitor device may include a sealed container. The sealed container may include a valve and a sorbent material. The valve may be effective to selectively expose the sorbent material to an environment outside of the container. The thermoelectric heater may be in thermal communication with the membrane. The power source may be in communication with the membrane. The current measuring device may be in communication with the membrane. The processor may be in communication with the valve, the thermoelectric heater, the power source and the current measuring device. The processor may be effective to control the valve to open so that the membrane sorbs an analyte from the air. The processor may be effective to control the valve to close. The processor may be effective to control the power source to apply a voltage across the membrane. The processor may be further effective to control the current measuring device to detect a current through the membrane while the voltage is applied across the membrane. The processor may be effective to determine a fingerprint of the membrane with the analyte based on the voltage and current. The processor may be effective to subtract the fingerprint from a fingerprint of the membrane to determine a fingerprint of the analyte. The processor may be further effective to compare the fingerprint of the analyte with a library of fingerprints to identify the analyte.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 5 is a block diagram illustrating an example computing device that is arranged to use an inelastic electron tunneling air monitor;

Figure 1:
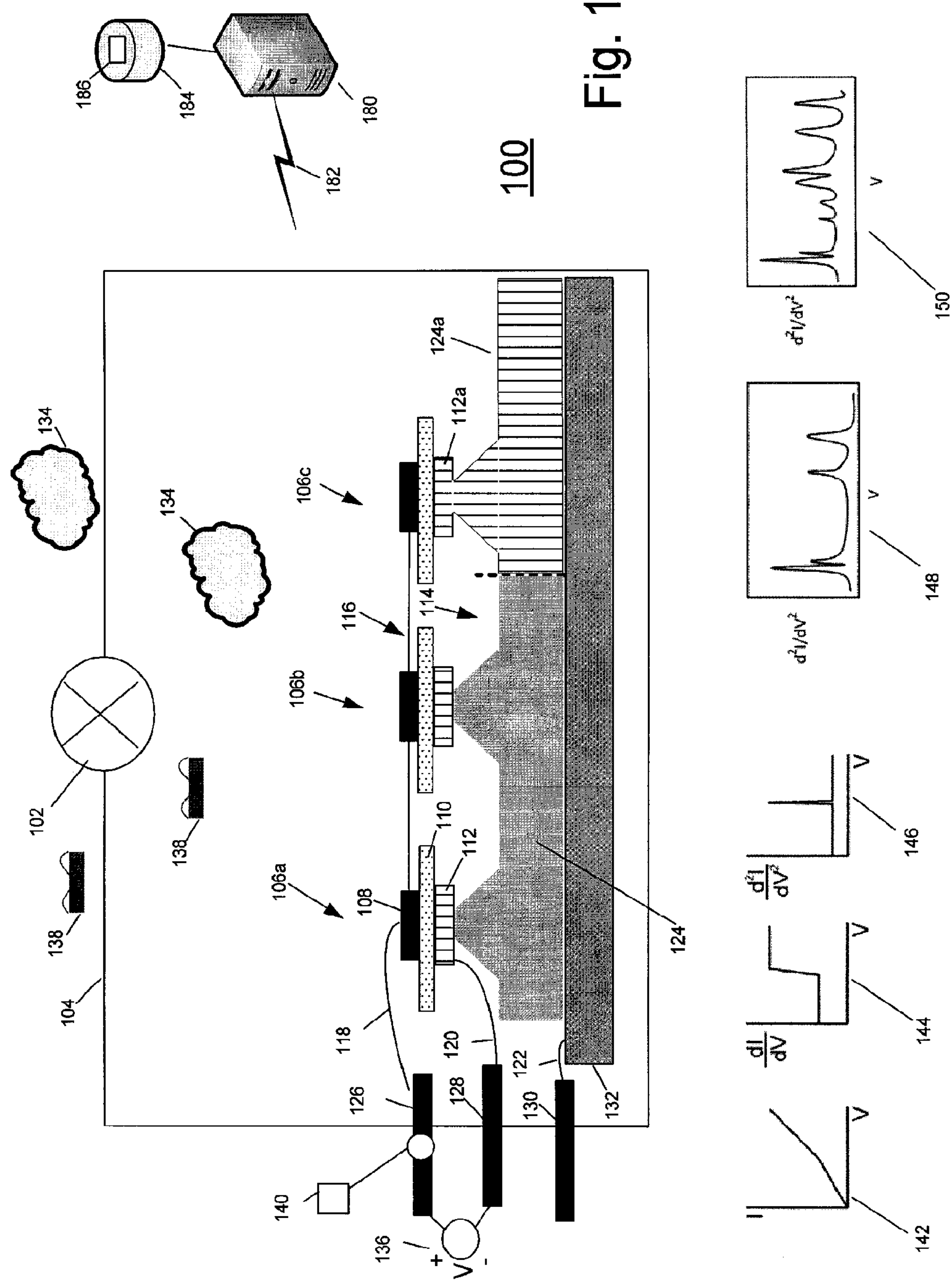
FIG. 1 illustrates a side view of an example system that can be used to implement an inelastic electron tunneling air monitor.

all arranged according to at least some embodiments described herein.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

This disclosure is generally drawn, among other things, to systems, methods, materials and apparatus related to an inelastic electron tunneling air monitor.

Briefly stated, technologies are generally described for an air monitoring device, a method for forming an air monitoring device, and methods and systems for monitoring air using an air monitoring device. A method of forming an air monitor device may include placing a sorbent membrane on a material of n type conductivity. The method may further include placing an electrode on the membrane and placing a thermoelectric heater in thermal communication with the membrane. The method may further include placing the membrane, material, and electrode in a sealed container including a valve to form the air monitor device. The valve may be effective to selectively expose the membrane to an environment outside of the container.

It will also be understood that any compound, material or substance which is expressly or implicitly disclosed in the specification and/or recited in a claim as belonging to a group or structurally, compositionally and/or functionally related compounds, materials or substances, includes individual representatives of the group and all combinations thereof.

Figure 2:
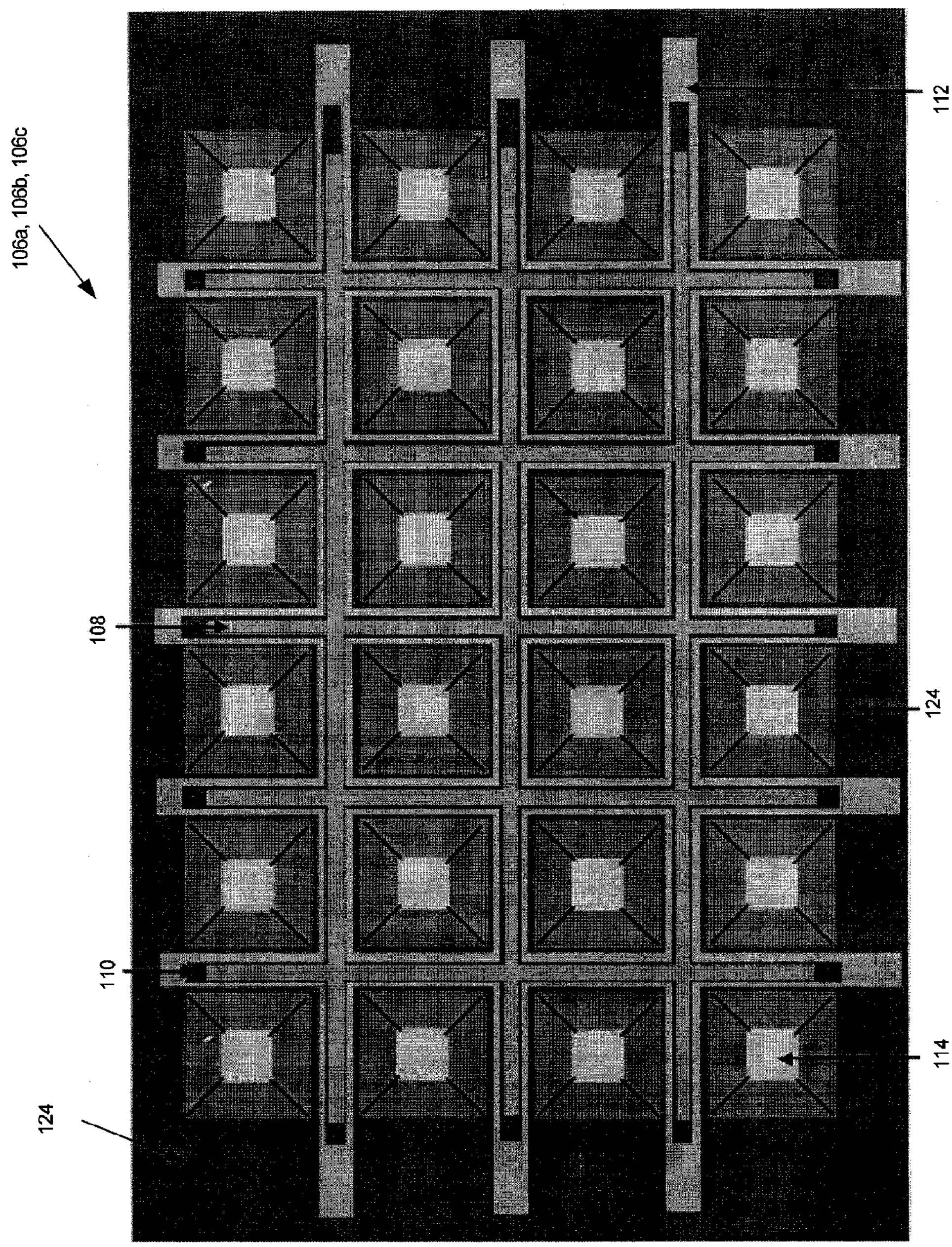
FIG. 2 illustrates a top view of an example system that can be used to implement an inelastic electron tunneling air monitor.

FIG. 1 illustrates a side view of an example system that can be used to implement an inelastic tunneling air monitor in accordance with at least some embodiments described herein. FIG. 2 illustrates a top view of an example system that can be used to implement an inelastic tunneling air monitor in accordance with at least some embodiments described herein.

An example inelastic electron tunneling air monitor system 100 may include a chamber 104 and/or a power source 136. Chamber 104 may include one or more devices 106*a*, 106*b*, 106*c*, a substrate 124, a thermoelectric heater 132, and/or leads 126, 128 and/or 130. At least some of these elements may be arranged in communication with a processor 180 through a communication link 182. As discussed in more detail below, system 100 may be used to analyze an analyte in air outside container 104 such as a gas 134 and/or liquid 138. In some examples, processor 180 may be adapted in communication with a memory 184 that may include instructions 186 stored therein. Processor 180 may be configured, such as by instructions 186, to control at least some of the operations/actions/functions described below.

Focusing on device 106*a* as an example of devices 106*a*, 106*b*, 106*c*, device 106 may include a top electrode 108, a sorbent membrane 110 and a well 112. Top electrodes 108 of devices 106 may be brought to substantially the same voltage potential through wires 116. Well 112 may be made of a material with an n or n+ type conductivity. In this example, substrate 124 may be, for example, a silicon wafer or other wafer with a p type conductivity as shown for devices 106*a* and 106*b*. In another example shown at 106*c*, well 112*a* and substrate 124*a* may both be made of a material with an n or n+ type conductivity. Well 112 may be used to inject electrons into membrane 110 as is explained in more detail herein. Membrane 110 may be a porous sorbent polymer such as a simple aliphatic polymer like polyethylene and polypropylene, a fluorinated aliphatic polymer like polytetrafluoroethylene, or other absorbing materials such as polystyrene, polystyrene sulfonate, polyethylene glycol, polyethylene oxide, polyethylene terephthalate, polyvinylalcohol, polymethylacrylate, polybutylacrylate. Membrane 110 may be made of a material effective to adsorb, absorb, and/or liberate an analyte such as liquid 138 or gas 134.

To form devices 106*a*, 106*b*, 106*c*, in examples where substrate 124 is of a p type conductivity, devices 106*a*, 106*b*,

106*c*, may be formed by doping areas of substrate 124 with n+ traces to form wells 112. In examples where substrate 124 is of an n type conductivity, substrate 124 may be etched to include well 112. Membrane 110 may be plasma treated, such as by exposure to an inert gas like argon, oxygen, nitrogen, hydrogen etc., to make membrane 110 porous. Membrane 110 may be spin coated onto well 112. For example, membrane 110 may be spun coated in a molten or solvated state and then dried and cured. In an example, membrane 110 may have a thickness of about 1 nm to about 10 nm. Top electrode 108 may be evaporated or sputtered onto membrane 110. In an example, top electrode 108 may be made of aluminum or other conductive material.

During the formation of devices 106*a*, 106*b*, 106*c*, trenches 114 may be formed in substrate 124. For example, alkali hydroxide anisotropic etching may be used to form trenches 114. A mask may be used in a photolithographic process to etch substrate 124 and form trenches 114. In an example, wet etching, gas etching, deep reactive ion etching, etc. could be used to form trenches 114. Trenches 114 may have pyramidal shape. For example, trenches may be formed after electrode 108 is deposited on membrane 110 such as in a wet or dry etching where silicon is etched but an organic or polymer on a surface is not etched. Trenches 114 may provide additional paths for an analyte such as gas 134 and/or liquid 138 to reach and be sorbed by membrane 110. The analyte may reach membrane 110 from a top or bottom of container 104.

Devices 106*a*, 106*b*, 106*c* may be placed in thermal communication with thermoelectric heater 132 and the combination, with or without heater 132, may be sealed in container 104. Container 104 may be hermetically sealed and may be made of a material with a relatively low thermal expansion, such as a coefficient of thermal expansion of less than about 15 ppm/degree Celsius and a relatively high thermal conductivity, such as greater than about 10 W/mK. For example, container 104 may be made of an alloy such as Fe—Ni Alloy 42, an iron nickel cobalt alloy from KOVAR, Cu—W, Mo, or a ceramic such as AlN and BeO. Leads 126, 128, 130 may be sealed in container 104 and may extend partially inside and partially outside container 104.

A wire 118 may communicate electrode 108 and lead 126. A wire 120 may communicate well 112 and lead 128. In examples where substrate 124 and well 112 are both made of an n type conductivity material (as shown at 124*a* and 112*a*), wire 120 may communicate well 112*a* and lead 128. A wire 122 may communicate thermoelectric heater 132 and lead 130.

Power source 136 may be placed in communication with leads 126 and 128. Power source 136 may be controlled to apply a series of voltages across well 112, 112*a* and electrode 108. Power source 136 may be effective to inject electrons from well 112, 112*a* and/or from electrode 108 into membrane 110. In an example, power source 136 may scan through about 0 volts to about 50 volts in microvolt or single volt increments. A current measuring device 140 may measure a current through electrode 108 and/or well 112, 112*a* while power source 136 applies voltage across well 112, 112*a* and electrode 108. Voltage across well 112, 112*a* and electrode 108, and current measured through devices 106*a*, 106*b*, 106*c*, may be sent to a processor, such as processor 180.

Processor 180 may be configured to determine a voltage versus current curve 142. Curve 142 may be indicative of a vibrational spectrum of the material in between electrode 108 and well 112, 112*a*. This material may include membrane 110 and may include an analyte such as gas 134 or liquid 138. Processor 180 may further be able to determine a curve 144 indicating a first derivative of the current with respective to voltage. Processor 180 may further be able to determine a curve 146 indicating a second derivative of the current with respective to voltage. Curve 146 may provide a fingerprint of membrane 110 which may also include an analyte such as gas 134 and/or liquid 138. Non-absorbed, or elastically tunneling electrons through membrane 110 may produce a single voltage versus current slope. Absorbed or inelastically tunneling electrons that resonate at a particular molecular vibration mode in membrane 110 may manifest in an increase of absorbed current. This may result in a slope change in curve 142 so that the second derivative of the current with respect to voltage may provide a fingerprint of membrane 110. Processor 180 may compare curve 146 with other curves in a library, such as in memory 184, to identify gas 134 or liquid 138.

In operation, as discussed herein, system 100 may be used to generate a fingerprint of the material between electrode 108 and well 112, 112*a*. System 100 may be first be used to generate a fingerprint of membrane 110 alone so that this fingerprint may later be subtracted from subsequently determined fingerprints including analytes. Processor 180 may be configured to control valve 102 to open and control thermoelectric heater to heat membrane 110 to liberate at least some substances out of membrane 110. For example, processor 180 may control thermoelectric heater 132 to heat membrane 110 to about 40 degrees Celsius to about 90 degrees Celsius for a time period of about one minute to about ten minutes. Membrane 110 may liberate materials in membrane 110 through valve 102.

Processor 180 may then control valve 102 to close. Processor 180 may control thermoelectric heater 132 to cool membrane 110 to a temperature of about −10 degrees Celsius to about −40 degrees Celsius. Processor 180 may control power source 136 to scan a voltage across substrate 124, or well 112, and electrode 108. Processor 180 may control current measuring device 140 to detect a current through membrane 110. Processor 180 may receive a voltage versus current curve for membrane 110 alone. Processor 180 may also determine the first and second derivatives of current with respect to voltage of these curves to determine a fingerprint 148 for membrane 110 alone.

Processor 180 may then control thermoelectric heater 132 to allow container 104 to return to ambient temperature. Processor 180 may then control valve 102 to open and allow gas 134 or liquid 138 to enter container 104. Processor 180 may control valve 102 to remain open for a time period of about 5 minutes to about 5 hours. Processor 180 may then control valve 102 to close. Processor 180 may control thermoelectric heater 132 to cool membrane 110 to a temperature of about −10 degrees Celsius to about −40 degrees Celsius. Processor 180 may control power source 136 to scan a voltage across well 112, 112*a* and electrode 108. Processor 180 may control current measuring device 140 to detect a current through membrane 110 including gas 134 or liquid 138. Processor 180 may receive a voltage versus current curve for membrane 110 with gas 134 or liquid 138. Processor 180 may also determine the first and second derivatives of current with respect to voltage of these curves to determine a fingerprint 150 for membrane 110 with gas 134 or liquid 138. Processor 180 may then subtract the fingerprint 148 for membrane 110 for fingerprint 150 to determine a fingerprint for gas 134 or liquid 138. Processor 180 may compare this fingerprint with a library of fingerprints in memory 184 to determine the analyte including gas 134 or liquid 138.

Among other benefits, a system arranged in accordance with the present disclosure may be used to form and use an inelastic electronic tunneling air monitor. For example, an atmospheric gas sensor may be formed. A relatively compact sensor may be formed that may be used to evaluate samples of air or a liquid such as volatile organic compounds like benzene, ethylbenzene, toluene, xylene, etc. A monitor may be packaged in an electronics assembly such as a silicon based mems (microelectromechanical system). A microchip may be produced including an air sensor.

Figure 3:
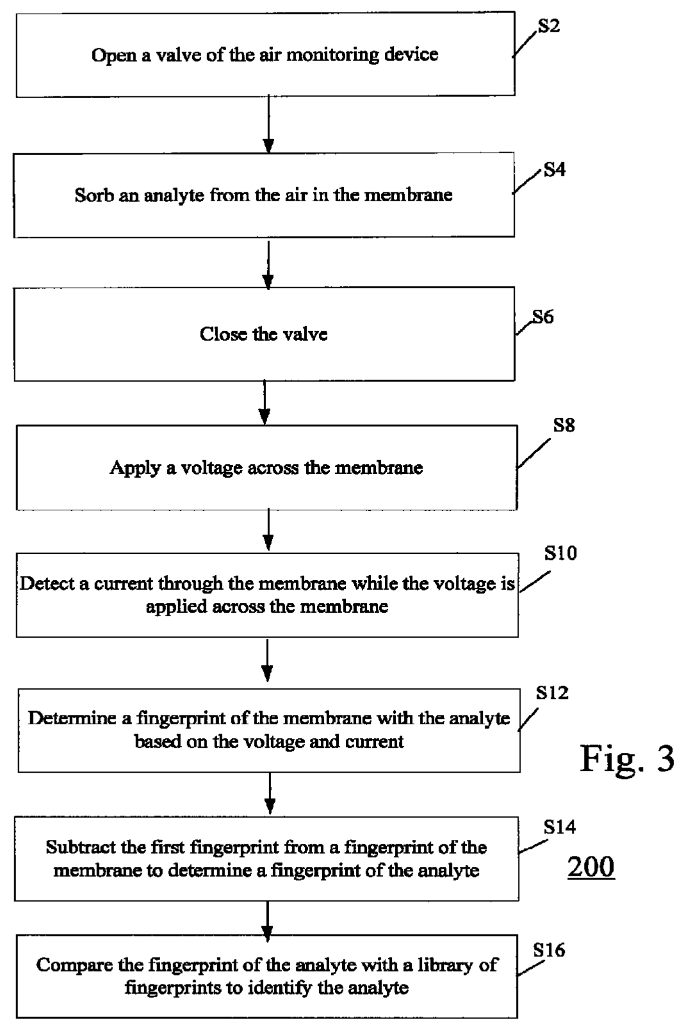
FIG. 3 depicts a flow diagram for an example process for using an inelastic electron tunneling air monitor.

FIG. 3 depicts a flow diagram for an example process 200 for using an inelastic electron tunneling air monitor in accordance with at least some embodiments described herein. The process in FIG. 3 could be implemented using, for example, system 100 discussed above. An example process may include one or more operations, actions, or functions as illustrated by one or more of blocks S2, S4, S6, S8, S10, S12, S14 and/or S16. Although illustrated as discrete blocks, various blocks may be divided into additional blocks, combined into fewer blocks, or eliminated, depending on the desired implementation.

Process 200 may begin at block S2, "Open a valve of the air monitoring device." At block S2, a processor may control a valve of an air monitoring device to open to expose the air monitoring device to an environment including an analyte.

Processing may continue from block S2 to block S4, "Sorb an analyte from the air in the membrane." At block S4, an analyte may be sorbed from the air into the membrane.

Processing may continue from block S4 to block S6, where the processor may close the valve. Processing continue from block S6 to block S8, where the processor may control a voltage to be applied across the membrane. Processing may continue from block S8 to block S10, "Detect a current through the membrane while the voltage is applied across the membrane." At block S10, a current may be detected through the membrane while the voltage is applied.

Processing may continue from block S10 to block S12, "Determine a fingerprint of the membrane with the analyte based on the voltage and current." At block S12 a fingerprint of the membrane with the analyte may be determined. For example, the processor may first determine a fingerprint of the membrane alone and then determine a fingerprint of the membrane with the analyte. The fingerprint may be determined by, for example, determining a second derivative of the current through with respect to the voltage across the membrane.

Processing may continue from block S12 to block S14, where the processor may subtract a fingerprint of the combination of the analyte and membrane from a fingerprint of the membrane to determine a fingerprint of the analyte. Processing may continue from block S14 to block S16 where the processor may compare the fingerprint of the analyte with a library of fingerprints to identify the analyte.

In an example, an air sensor may include a silicon substrate with doped wells. The sensor may start with a silicon wafer. A membrane may be fabricated by solution spin casting of an aliphatic polymer such as polyethylene or polypropylene. Onto the membrane may be sputtered or evaporated the top electrode with a metal such as aluminum. Openings in the membranes can be cut using focused laser machining or by photolithography. For photolithography, a photoresist may be applied, exposed and developed such that a protective layer exists on the membrane-electrode material. The protective layer may remain on the membrane. The open areas of the photoresist may allow an acid or base etch to remove the metal electrode. An organic solvent etch may be used to remove unwanted membrane material. With the photoresist pattern still intact, the structure may then be exposed to an anisotropic silicon etch such as potassium hydroxide (KOH) to etch pyramidal trenches. Once the etch is complete, the photoresist may be dissolved away and the wafer may be cleaned. The wafer may then be cut to simulate an individual die that includes an array of some number of sensor elements. The die may then mounted and wire-bonded into a hermetic package that allows the ingress and release of air. The package can include a steel "can" type package fitted with a valve that will be controlled to open or close the "can" to the ambient environment. This steel can may then mounted onto the thermoelectric element that is responsible for cooling and heating of the whole package.

Figure 4:
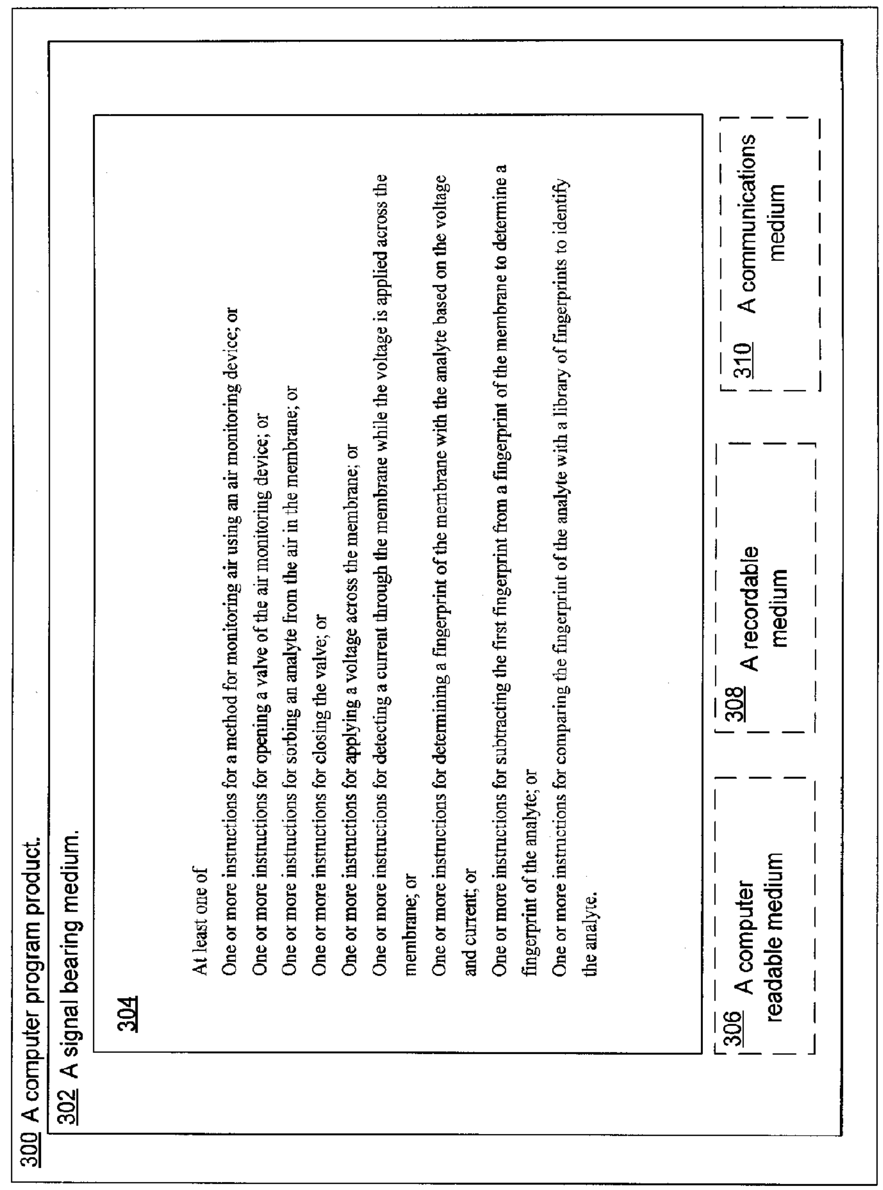
FIG. 4 illustrates a computer program product to use an inelastic electron tunneling air monitor.

FIG. 4 illustrates a computer program product to use an inelastic electron tunneling air monitor in accordance with at least some embodiments described herein. Program product 300 may include a signal bearing medium 302. Signal bearing medium 302 may include one or more instructions 304 that, when executed by, for example, a processor, may provide the functionality described above with respect to FIGS. 1-3. Thus, for example, referring to system 100, processor 180 may undertake one or more of the blocks shown in FIG. 4 in response to instructions 304 conveyed to the system 100 by medium 302.

In some implementations, signal bearing medium 302 may encompass a computer-readable medium 306, such as, but not limited to, a hard disk drive, a Compact Disc (CD), a Digital Video Disk (DVD), a digital tape, memory, etc. In some implementations, signal bearing medium 302 may encompass a recordable medium 308, such as, but not limited to, memory, read/write (R/W) CDs, R/W DVDs, etc. In some implementations, signal bearing medium 302 may encompass a communications medium 310, such as, but not limited to, a digital and/or an analog communication medium (e.g., a fiber optic cable, a waveguide, a wired communications link, a wireless communication link, etc.). Thus, for example, program product 300 may be conveyed to one or more modules of the system 100 by an RF signal bearing medium 302, where the signal bearing medium 302 is conveyed by a wireless communications medium 310 (e.g., a wireless communications medium conforming with the IEEE 802.11 standard).

FIG. 5 is a block diagram illustrating an example computing device that is arranged to use an inelastic electron tunneling air monitor according to at least some embodiments described herein. In a very basic configuration 402, computing device 400 typically includes one or more processors 404 and a system memory 406. A memory bus 408 may be used for communicating between processor 404 and system memory 406.

Depending on the desired configuration, processor 404 may be of any type including but not limited to a microprocessor (μP), a microcontroller (μC), a digital signal processor (DSP), or any combination thereof. Processor 404 may include one more levels of caching, such as a level one cache 410 and a level two cache 412, a processor core 414, and registers 416. An example processor core 414 may include an arithmetic logic unit (ALU), a floating point unit (FPU), a digital signal processing core (DSP Core), or any combination thereof. An example memory controller 418 may also be used with processor 404, or in some implementations memory controller 418 may be an internal part of processor 404.

Depending on the desired configuration, system memory 406 may be of any type including but not limited to volatile memory (such as RAM), non-volatile memory (such as ROM, flash memory, etc.) or any combination thereof. System memory 406 may include an operating system 420, one or more applications 422, and program data 424. Application 422 may include an air monitoring algorithm 426 that is arranged to perform the various functions/actions/operations as described herein including at least those described with respect to system 100 of FIGS. 1-4. Program data 424 may include air monitoring data 428 that may be useful for using an inelastic electron tunneling air monitor as is described herein. In some embodiments, application 422 may be arranged to operate with program data 424 on operating system 420 such that an inelastic tunneling air monitor may be provided. This described basic configuration 402 is illustrated in FIG. 4 by those components within the inner dashed line.

Computing device 400 may have additional features or functionality, and additional interfaces to facilitate communications between basic configuration 402 and any required devices and interfaces. For example, a bus/interface controller 430 may be used to facilitate communications between basic configuration 402 and one or more data storage devices 432 via a storage interface bus 434. Data storage devices 432 may be removable storage devices 436, non-removable storage devices 438, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 406, removable storage devices 436 and non-removable storage devices 438 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 400. Any such computer storage media may be part of computing device 400.

Computing device 400 may also include an interface bus 440 for facilitating communication from various interface devices (e.g., output devices 442, peripheral interfaces 444, and communication devices 446) to basic configuration 402 via bus/interface controller 430. Example output devices 442 include a graphics processing unit 448 and an audio processing unit 450, which may be configured to communicate to various external devices such as a display or speakers via one or more A/V ports 452. Example peripheral interfaces 444 include a serial interface controller 454 or a parallel interface controller 456, which may be configured to communicate with external devices such as input devices (e.g., keyboard, mouse, pen, voice input device, touch input device, etc.) or other peripheral devices (e.g., printer, scanner, etc.) via one or more I/O ports 458. An example communication device 446 includes a network controller 460, which may be arranged to facilitate communications with one or more other computing devices 462 over a network communication link via one or more communication ports 464.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 400 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 400 may also be implemented as a personal computer including both laptop computer and non-laptop computer configurations.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of forming an air monitor device, the method comprising:
- placing a sorbent polymer membrane on a material of n type conductivity;
- placing an electrode on the membrane;
- placing a thermoelectric heater in thermal communication with the membrane; and
- placing the membrane, material, and electrode in a sealed container including a valve to form the air monitor device, the valve effective to selectively expose the membrane to an environment outside of the container.

2. The method of claim 1, wherein the membrane includes polyethylene and polypropylene or polytetrafluoroethylene.

3. The method of claim 1, wherein the material is a first material of n+ conductivity and the method further comprises:
- placing the first material on a second material of p type conductivity; and
- making a trench in the second material to expose part of the membrane.

4. The method of claim 1, wherein the material is a first material of n+ conductivity and the method further comprises:
- placing the first material on a second material of p type conductivity; and
- etching a trench in the second material to expose part of the membrane using alkali hydroxide anisotropic etching.

5. The method of claim 1, further comprising, prior to placing the sorbent membrane on the material of n type conductivity, exposing the membrane to a gas to make the membrane porous.

6. An air monitor device comprising:
- a sorbent polymer membrane on a material of n type conductivity;
- an electrode on the membrane;
- a thermoelectric heater in thermal communication with the membrane; and
- the membrane, n type material, and electrode in a sealed container, wherein the sealed container includes a valve effective to selectively expose the membrane to an environment outside of the container.

7. The device of claim 6, wherein the membrane includes polyethylene and polypropylene or polytetrafluoroethylene.

8. The device of claim 6, wherein the container is made of a Fe—Ni Alloy 42, an iron nickel cobalt alloy, Cu—W, Mo, or BeO.

9. The device of claim 6, further comprising:
- a first lead, wherein the first lead extends partially inside and partially outside the container;
- a second lead, wherein the second lead extends partially inside and partially outside the container;
- a first wire in communication with the electrode and the first lead; and
- a second wire in communication with the n type material and the second lead.

10. The device of claim 6, further comprising:
- a first lead, wherein the first lead extends partially inside and partially outside the container;
- a second lead, wherein the second lead extends partially inside and partially outside the container;
- a first wire in communication with the electrode and the first lead;
- a second wire in communication with the n type material and the second lead;
- a power source in communication with the first lead and the second lead;
- a current measuring device in communication with at least one of the first lead and the second lead; and
- a processor in communication with the power source and the current measuring device.

11. The device of claim 6, wherein the material is a first material of n+ conductivity and the device further comprises the first material on a second material of p type conductivity.

12. The device of claim 6, wherein the material is a first material of n+ conductivity and the device further comprises:
- the first material on a second material of p type conductivity; and
- a trench in the second material, wherein the trench is effective to expose part of the membrane.

13. A method for monitoring air using an air monitoring device, the method comprising:

opening a valve of the air monitoring device;

heating a sorbent membrane of the air monitoring device sufficient to at least partially liberate a substance in the membrane;

closing the valve;

applying a first voltage across the membrane;

detecting a first current through the membrane while the first voltage is applied across the membrane;

determining a first fingerprint of the membrane based on the first voltage and first current;

opening the valve;

sorbing an analyte from the air in the membrane;

closing the valve;

applying a second voltage across the membrane;

detecting a second current through the membrane while the second voltage is applied across the membrane;

determining a second fingerprint of the membrane with the analyte based on the second voltage and second current;

subtracting the first fingerprint from the second fingerprint to determine a third fingerprint of the analyte; and comparing the third fingerprint of the analyte with a library of fingerprints to identify the analyte.

14. The method of claim 13, wherein the membrane is a polymer.

15. The method of claim 13, wherein the membrane includes polyethylene and polypropylene or polytetrafluoroethylene.

16. The method of claim 13, wherein the container is made of a Fe—Ni Alloy 42, an iron nickel cobalt alloy, Cu—W, Mo, or BeO.

17. The method of claim 13, wherein:

the sorbent membrane is on a material of n type conductivity;

an electrode is on the membrane;

a thermoelectric heater is in thermal communication with the membrane; and wherein the membrane, material, and electrode are in a sealed container including the valve.

18. The method of claim 13, wherein:

the sorbent membrane is on a first material of n+ type conductivity;

an electrode is on the membrane;

the first n+ type material is on, or doped within, a second material of p type conductivity;

a thermoelectric heater is in thermal communication with the membrane; and the membrane, material, and electrode are in a sealed container including the valve.

19. The method of claim 13, wherein:

the sorbent membrane is on a first material of n+ type conductivity;

an electrode is on the membrane;

the first n+ type material is on, or doped within a second material of p type conductivity;

a trench in the second material is effective to expose part of the membrane;

a thermoelectric heater is in thermal communication with the membrane; and the membrane, material, and electrode in a sealed container including the valve.

* * * * *